United States Patent [19]

Targowski et al.

[11] 4,220,413
[45] Sep. 2, 1980

[54] AUTOMATIC GAS FLOW CONTROL APPARATUS FOR AN ATOMIC ABSORPTION SPECTROMETER BURNER

[75] Inventors: Roger W. Targowski, Fairfield; Chester G. Fisher, III, Southport, both of Conn.

[73] Assignee: The Perkin-Elmer Corporation, Norwalk, Conn.

[21] Appl. No.: 35,583

[22] Filed: May 3, 1979

Related U.S. Application Data

[63] Continuation of Ser. No. 907,449, May 22, 1978, abandoned.

[51] Int. Cl.$^2$ ............................ G01J 3/30; F23N 3/08
[52] U.S. Cl. ..................................... 356/315; 431/18; 431/126
[58] Field of Search ................ 356/315, 417; 431/4, 431/18, 126

[56] References Cited

U.S. PATENT DOCUMENTS

| | | | |
|---|---|---|---|
| 2,847,899 | 8/1958 | Walsh | 356/315 |
| 3,516,771 | 6/1970 | Rendina | 431/126 |
| 3,525,476 | 8/1970 | Boling et al. | 239/338 |
| 3,583,844 | 6/1971 | Smith, Jr. | 356/315 X |
| 3,689,225 | 9/1972 | White | 356/315 X |
| 3,806,250 | 4/1974 | George | 356/315 |
| 4,125,225 | 11/1978 | Venghiattis | 239/338 |

OTHER PUBLICATIONS

Barnett, *Analytical Chemistry*, vol. 44, No. 4, Apr. 1972, pp. 695–698.

*Primary Examiner*—F. L. Evans
*Attorney, Agent, or Firm*—S. A. Giarratana; F. L. Masselle; E. T. Grimes

[57] ABSTRACT

There is described a programmable gas flow control apparatus for use in atomic absorption spectroscopy. Essentially, an all pneumatic system is described which provides for a predetermined flow of fuel and oxidant to the burner. The invention compensates for the variation in oxidant flow due to nebulizer adjustments by adjusting the oxidant flow to the auxiliary inlet of the burner. The invention utilizes a pneumatic computing relay which senses the oxidant flow to the nebulizer and simultaneously adjusts the flow to the auxiliary inlet so that the total flow of oxidant satisfies the predetermined optimum rate. The constant monitoring of the nebulizer line by the computing relay allows for continual adjustment of the oxidant flow to offset subsequent adjustments.

12 Claims, 2 Drawing Figures

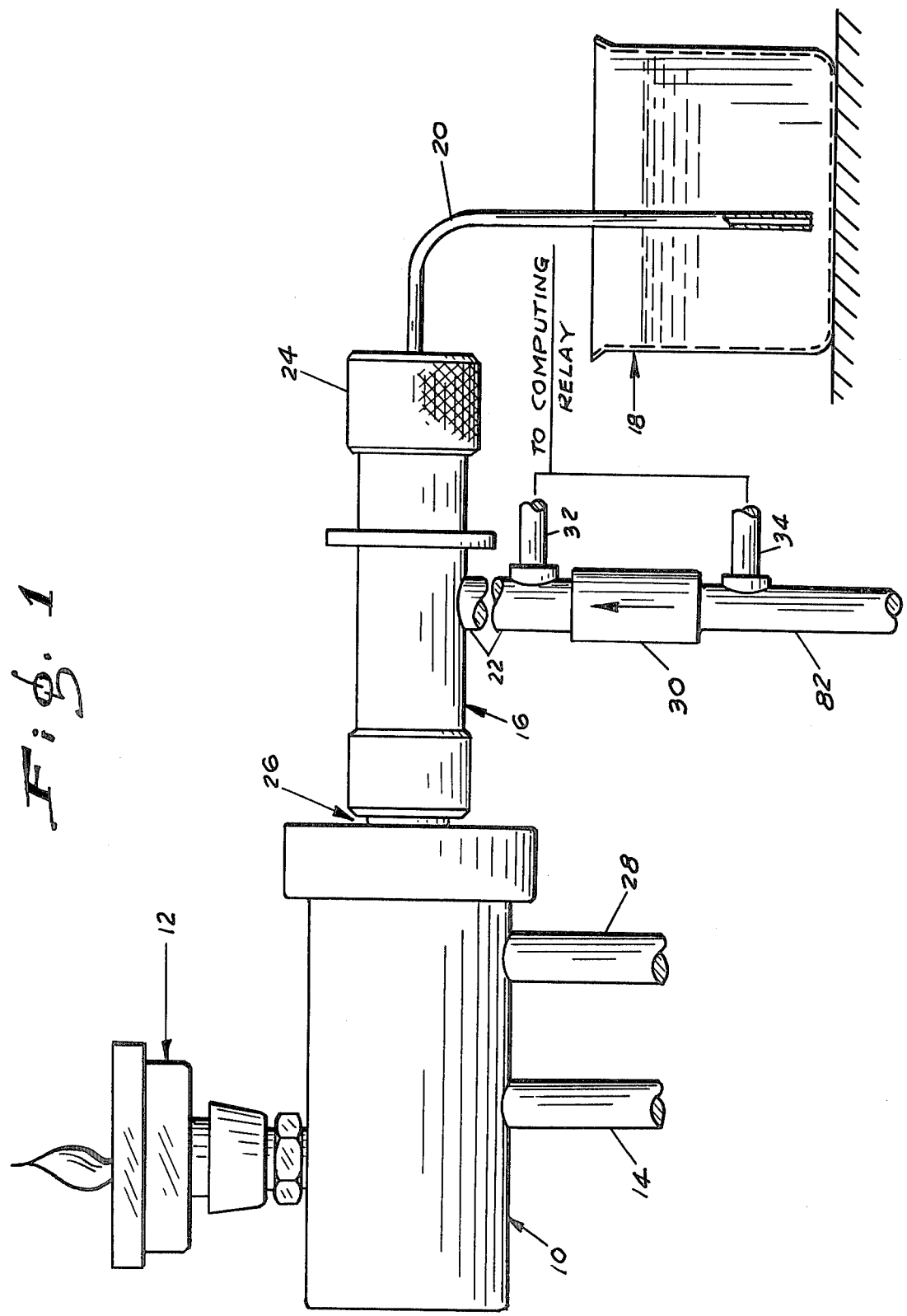

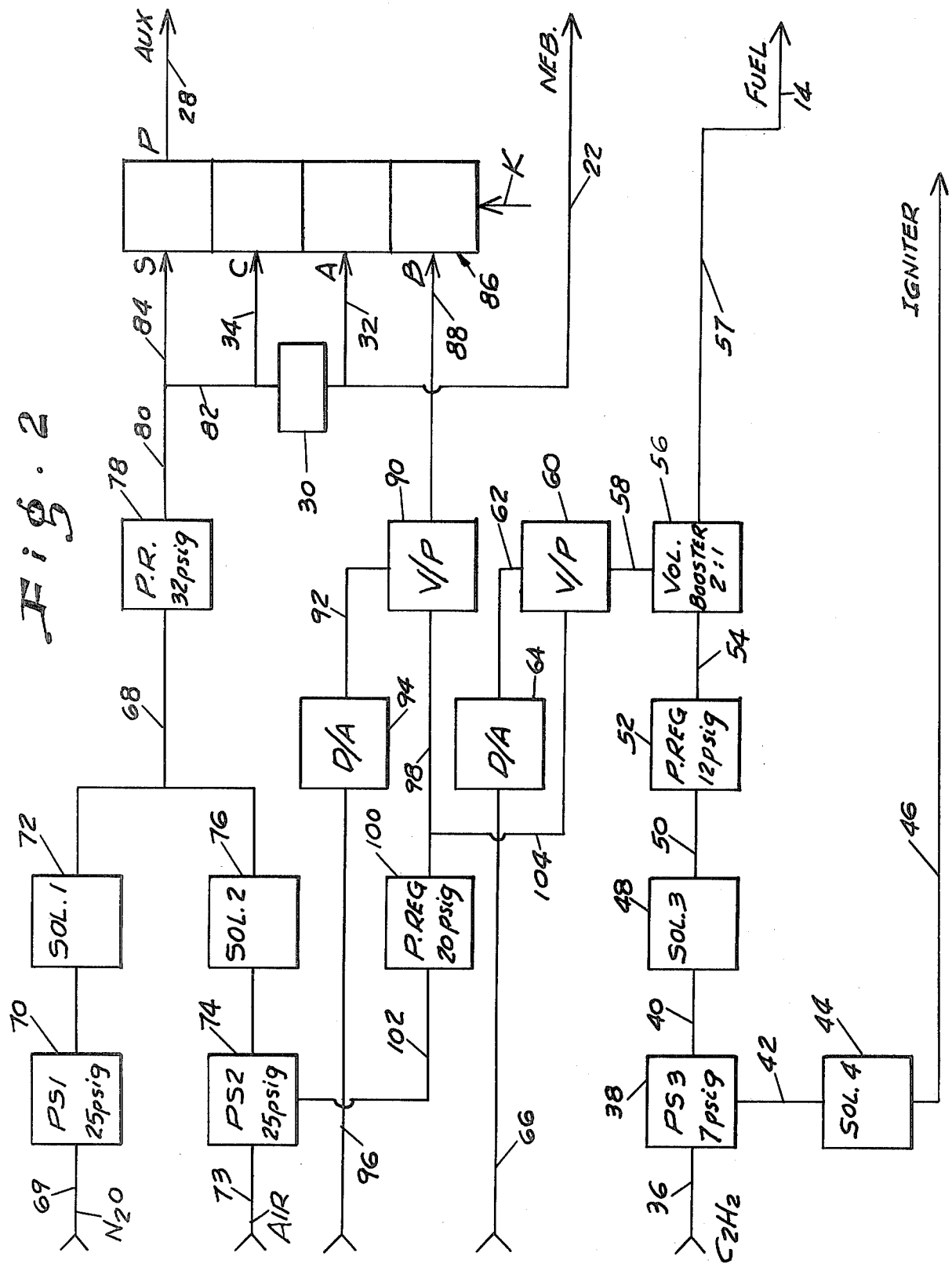

AUTOMATIC GAS FLOW CONTROL APPARATUS FOR AN ATOMIC ABSORPTION SPECTROMETER BURNER

This is a continuation of application Ser. No. 907,449, filed May 22, 1978, now abandoned.

FIELD OF THE INVENTION

This invention pertains generally to atomic absorption spectrometers, and more particularly, to an automatic gas control system for burners used in atomic absorption spectroscopy.

BACKGROUND OF THE INVENTION

In atomic absorption spectroscopy (see, for example, U.S. Pat. No. 2,847,899), the measurement of the absorption of a radiation beam at a characteristic resonant spectral line for a particular element yields a measure of the concentration of that element in an original sample solution. Presently, the most common technique for atomizing an element for purposes of the absorption measurement, is by introducing a liquid sample solution of the element of interest into a gas burner wherein droplets of the solution are vaporized and the elements ultimately atomized, so as to form in the path of the apparatus radiation beam, a substantial quantity of the element of interest in its atomic state.

In order to effect appropriate burning of the element-containing solution, the liquid must be converted into a fine spray and then mixed with a fuel and oxidant gas before introduction into the burner. The fine spray is achieved through use of a nebulizer, such as described in pending application, U.S. Ser. No. 634,587, filed Nov. 24, 1975, now U.S. Pat. No. 4,125,225, also assigned to the assignee herein.

A nebulizer, generally, employs a venturi-type restriction which passes rapidly-moving gas (hereinafter referred to as an oxidant) past an opening, drawing a portion of the liquid sample solution into the gas stream, effecting an atomizing of the liquid in the process. The liquid is said to be aspirated by the venturi effect caused by the rapidly moving current of gas.

The sample laden gas or oxidant, then passes into the burner chamber where it is mixed with additional oxidant from an auxiliary inlet, and fuel such as acetylene. It is then introduced into the burner head where it is ignited.

The sensitivity of the absorption measurement is dependent on many factors, one of which being the flame condition of the burner. I.e., the leanness or richness of the fuel-oxidant mixture. Also, the sensitivity of the measurement requires the optimization of the setting of the nebulizer which varies the amount of liquid sample aspirated by the rapidly flowing gas. Because of the nature of the mechanism for aspirating more or less of the sample, namely varying the flow of oxidant through the venturi-type restriction, there is the obvious side effect on the flame condition which has a direct effect on the sensitivity of the measurement. In prior systems, the operator would have to go back to the auxiliary inlet to the burner and vary the oxidant flow through it to compensate for the last adjustment to the nebulizer and the effect thereof on the oxidant flow into the burner.

The object of an automatic gas control system, would be to eliminate these readjustments due to the adjustments of the nebulizer.

Further, an automatic gas control system should allow for the programmability of optimum analysis parameters. E.g., with respect to the field herein discussed, namely atomic absorption spectometry, the optimum fuel-oxidant flow rates, element wave lengths, fuel-oxidant characteristics, and the like,—parameters which could be optimized by the methods analyst in the lab—should be maintained constant for each measurement even on differing instruments. Desirably, the optimum values for these factors can be stored in a memory device, such as on magnetic cards, which can be used to program different instruments to insure optimum results.

It is therefore a primary object of this invention to provide an apparatus which will respond identically to pre-programmed optimum fuel-oxidant gas flow rates, irregardless of the instrument system in which employed.

It is another object of this invention to provide operator-free adjustment of the oxidant flow to the auxiliary inlet of a burner to offset the effects of nebulizer adjustments on the oxidant flow therethrough.

There is yet another object of the invention to provide a pneumatic control means for adjusting the oxidant flow to the auxiliary inlet in response to nebulizer adjustments.

It is still another object of this invention to provide a pneumatic correction means which both senses a change in the flow of oxidant to the nebulizer intake and corrects the flow of the oxidant to the auxiliary inlet in response to the sensed change to said nebulizer.

SUMMARY OF THE INVENTION

Towards the accomplishment of the above and other objects which will become apparent from the following discussion, there is described herein, an automatic gas control apparatus for use in an atomic absorption spectrometer instrument system including a burner for burning a mixture of fuel, oxidant and an unknown element-containing sample, which comprises a fuel supply means which provides a predetermined flow of fuel to the burner based on a stored electrical signal corresponding to a previously determined, optimum flow rate; a nebulizer, which introduces a variable amount of sample, the nebulizer being adjustable to vary the sample flow so as to optimize the measured signal of the spectrometer; variable (auxiliary) oxidant supply means, the flow through which can be varied so as to make up the difference between the predetermined total flow of oxidant required for a prescribed sensitivity of the spectrometer and the varying amount supplied by the sample introducing means because of the adjustment feature required to optimize the measured signal; means for measuring the flow of oxidant through both the sample introducing nebulizer and the variable oxidant supply means; and means for comparing the sensed oxidant flows to the previously determined oxidant flow required for a prescribed sensitivity, with means for adjusting the flow of oxidant to the variable oxidant supply means in response to the comparison so as to insure that the total flow of oxidant to the burner is maintained at the predetermined amount. Preferably, the apparatus is substantially, pneumatically controlled. Particularly, the means for sensing the two oxidant flow rates and comparing these to the predetermined total flow rate, is done by a pneumatically operated, computing relay which further includes means for responding to the comparison and adjusting the oxidant flow from its inlet to outlet port, the latter in turn supplying the variable oxidant means. The result is that the total amount of oxidant to the burner is maintained at the predetermined amount.

BRIEF DESCRIPTION OF THE DRAWINGS

FIG. 1 is an elevation view of a nebulizer-burner assembly, typically employed in atomic absorption spectrometer instrumentation.

FIG. 2 is a block diagram of the gas control system in accordance with the invention.

DESCRIPTION OF THE PREFERRED EMBODIMENT

Referring now to FIG. 1, there is shown a typical nebulizer-burner assembly used in atomic absorption spectroscopy. It includes a chamber 10 for mixing fuel, oxidant and the unknown element-containing sample. The chamber feeds the burner 12 which ignites the fuel, oxidant and sample mixture. Feeding the chamber is a fuel line 14 which supplies a suitable gas, e.g. acetylene, from a regulated source.

Axially connected to the chamber 10 is a nebulizer 16. The internal configuration of the nebulizer is not shown, but is understood to be operational in a manner similar to many such devices on the market. A typical configuration can be seen in U.S. Ser. No. 634,587, mentioned above. The nebulizer introduces a variable flow of the unknown element-containing sample into the mixing chamber.

The sample solution is contained in a beaker such as 18. Typically the sample is an unknown metallic element in solution. The aspirating action of the venturi-type restriction in the nebulizer draws solution out of the beaker through capillary tubing 20. The aspiration of the sample is achieved by rapidly-moving gas, typically traveling through the venturi restriction, which draws the solution into the nebulizer and atomizes it into a fine spray. The rapidly-moving gas enters the nebulizer via tubing 22. Generally, this gas is referred to as the oxidant. In a typical situation, it might be nitrous oxide or, air.

To adjust the nebulizer for most efficient sample aspiration, the operator of the equipment, for the unit shown, would turn knob 24. This would alter the flow of sample into the assembly, but because of the nebulizer design, there will be a corresponding effect on the flow of the oxidant entering the nebulizer through tubing 22. The adjustment of the nebulizer by the operator for an optimum measured signal in the spectrophotometer will vary from unit to unit, so that differing effects on the oxidant flow rate through tubing 22 will result. Since the amount of oxidant supplied to the burner is altered, the flame condition and thus the signal measurement would be altered except for the present invention.

The nebulizer, typically, is axially joined to the mixing chamber by a sealing interface at 26.

Connected to the mixing chamber is a variable (auxiliary) supply of oxidant. This is provided through tubing 28. As will be seen hereafter in the discussion of FIG. 2, the amount of oxidant supplied at this point will be equal to the difference between the total flow of oxidant predetermined, for example, by a methods analyst as necessary to insure a prescribed sensitivity, and the varying amount supplied to the chamber by the nebulizer.

In order to sense the flow of oxidant supplied to the nebulizer, in-line means, such as a restrictor, is inserted in the oxidant supply tubing 22. The restrictor is shown at 30.

The flow rate is sensed by monitoring the pressure on either side of the restrictor. This is accomplished by pressure monitoring ports 32 and 34, connected into the tubing 22 and 82 respectively. For the indicated flow direction for the oxidant, the pressure at terminal 34 would be higher than the pressure at 32.

Ports 32 and 34 are shown as being directed to a so-called "computing relay" whose operation as it concerns the gas flow control system of the invention will be discussed with respect to FIG. 2. Generally, its function is to compare the pressure differential across the restrictor 30 to a predetermined command pressure based on a prescribed sensitivity of the spectrometer and to adjust the oxidant flow between the auxiliary inlet (hereinabove referred to as inlet 28) and the nebulizer inlet (hereinabove referred to as inlet 22) to compensate for the variations of oxidant flow in 22 due to nebulizer adjustments at knob 24.

Referring now to FIG. 2, there is shown in block diagram form, an arrangement of the various pneumatic components which effect the purposes of the invention. The few situations where reference numerals are identical to those employed in FIG. 1, those are done to identify the same identical components or tubing even though in this latter figure they are a block diagram equivalent.

Considering the fuel supply section initially, the burner fuel, acetylene, is supplied to the system via tubing 36. Acetylene is employed because it is readily available and inexpensive. Tubing 36 is connected to a pressure switch 38 which senses a safe level before closing. Typically, the acetylene at the input might be on the order of 15 psig, and the threshold pressure of the switch 38 set at 7 psig. The switch directs the fuel to a pair of solenoids via tubing 40 and 42. The first such solenoid 44 is energized at start up and directs the fuel through tubing 46 to the igniter section of the burner. Once ignited, solenoid 44 is opened and the fuel is blocked from that passageway.

During subsequent burner operation, solenoid 48 is closed and the fuel directed therethrough to tubing 50 and pressure regulator 52. The output of the regulator 54, typically, would have a fuel gas pressure at 12 psig. This pressure level is the maximum that can be employed in the burner because of the instability of acetylene above that pressure.

The regulator is connected to a volume booster 56. A typical unit would be a model 20, manufactured by the Industrial Products Division of the Fairchild Company. It responds to a command pressure on line 58, in order to further reduce the pressure of the acetylene from 12 psig down to a value determined previously to be optimum for spectrometer sensitivity. For example, the pressure of the gas in tubing 57, typically, will be at 6 psig. The tubing 57 is connected to the fuel inlet duct 14 previously referred to in FIG. 1.

The command pressure input to the volume booster 56 is supplied by a voltage to pressure transducer 60. The latter receives an analog signal on input line 62 from a digital to analog converter 64. The D/A converter is supplied, via line 66, with a digital word permanently stored on a typical memory device such as a magnetic card or disc. The digital word represents the optimum flow of the fuel as previously determined by a methods analyst in arriving at optimum parameters for the system.

The volume booster, in a situation where acetylene is employed, for example, is a non-relieving type, i.e., it would bleed off the necessary amount of acetylene into the burner to achieve the commanded pressure differential and not into the air as might be the case with relieving-type boosters.

The analog signal appearing on line 62 to the transducer 60, typically, is on the order of 0 to 9 volts, with the corresponding pressure out of the transducer in tubing 58, between 3 and 15 psig. A typical transducer is model T5109, again manufactured by the Industrial Products Division of the Fairchild Company.

Thus there has been described means for supplying a predetermined flow rate of fuel for the burner in response to a pre-existing command. Thus optimization of a critical parameter is assured.

The total oxidant supply to the system appears in tubing 68 and uses as its source either a supply of nitrous oxide entering on line 69, through pressure switch 70 and solenoid 72, or air on line 73 through pressure switch 74 and solenoid 76. The pressure switches 70 and 74, typically, have a setting at 25 psig. Depending on the oxidant to be used, either solenoid 72 or 76 would be selected by appropriate control.

The oxidant in tubing 68 is supplied to a pressure regulator 78 which maintains a pressure level in tubing 80 at, typically, 32 psig. Tubing 80 is connected by a T-connection to tubing 82 and 84. Tubing 82 (previously referred to with respect to FIG. 1) is connected to restrictor 30. As discussed earlier, the down stream side of the restrictor is supplied to the oxidant inlet on the nebulizer via tubing 22.

86 refers to a pneumatic computing means, known typically as a computing relay. A standard unit is a model 22 computing relay as manufactured by the Industrial Products Division of Fairchild Company. It likewise generally, would be a non-relieving type. The computing relay includes an oxidant inlet port, S, and outlet port, P. These are connected, respectively, to tubing 84, the variable oxidant flow supply, and the auxiliary inlet 28, to the mixing chamber.

Further, the relay includes ports C and A which are connected respectively to the pressure monitoring ports on either side of the in-line restrictor 30.

Also, the computing relay includes a command pressure port B which is connected to a command pressure supply in line 88 which emanates from a voltage to pressure transducer 90. The latter provides a command pressure on its output from, typically, 3 to 15 psig in response to an analog signal of 0 to 9 volts, as received on input line 92. The analog signal is produced by a digital to analog converter 94 and is proportional to a predetermined digital word received on input electrical line 96. The digital word appearing on line 96 would be stored, much like the signal representing the predetermined fuel rate on a memory device such as a magnetic card or disc. Its value, again, would be previously determined by a methods analyst in arriving at optimum values for the various parameters necessary to be considered in optimizing the sensitivity of the instrument.

The input pressure supply for the voltage transducer 90, and the previously described transducer 60, is developed from an air supply line and is inputted to the transducer 90 on line 98. Line 98 is connected to a pressure regulator 100 which is connected by line 102 to the previously discussed pressure switch 74 on the air input line. The regulator 100 maintains the pressure in lines 98 and 104, the supply lines for the transducers, at an adequate pressure necessary for the command function performed by each. Typically, the pressure in those lines might be on the order of 20 psig.

The computing relay is a well known device which employs chambers and diaphragms to solve the equation $P = A + B - C + K$.

Where P is the pressure in the oxidant outlet port, A and C are the pressures on either side of the line restrictor, and B is the command pressure out of transducer 90.

K is an offset which is effected by a mechanical adjustment on the computing relay unit. It is set initially so as to assure at port P, a sufficient pressure to provide the lowest flow rate of oxidant in response to the lowest digital command on line 96.

The computing relay is thus seen to perform the function of sensing and comparing the flow of oxidant to the nebulizer and the auxiliary oxidant supply means to a predetermined command flow rate for the oxidant as represented by the pressure on line 88. The relay adjusts the flow of oxidant to the auxiliary inlet in response to this comparison and does so and continues to readjust the flow thereto as it senses variations in the flow to the nebulizer across the restrictor 30.

Other variations of the above embodiment would be apparent to those skilled in the art in light of the above. For example, instead of employing a computing relay, means for sensing the flow of oxidant to the sample introducing means (nebulizer), in oxidant supply line, 22, and as well as means sensing the flow in line 28 could be employed. These might, typically, produce electrical signals which would then be compared with the command electrical signal. Valves in each of the supply lines could be provided which would be operated upon by the compared electrical signals so as to vary the amount of oxidant flowing into the auxiliary based on the compared readings.

The advantage of the present technique, is that the computing relay can both sense the variations in oxidant flow to the nebulizer and effect an adjustment in accordance therewith to the oxidant flow to the auxiliary inlet.

The above described embodiment is not to be construed as limiting the extent and breadth of the invention which is defined in the appended claims.

What is claimed is:

1. A gas flow control system for an atomic absorption spectrometer having a burner for burning a mixture of fuel, oxidant and a sample comprising:
    means for supplying fuel to the burner,
    means for supplying sample to the burner including means for adjusting the supply of sample to optimize the measured signal of the spectrometer and first means for supplying oxidant to the burner, the supply of oxidant to the burner through said first means being adjustable in accordance with the adjustment to said sample adjustment means,
    second means for providing an adjustable supply of oxidant to the burner, the total supply of oxidant to the burner being equal to the sum of the oxidant supplied to the burner by said first and second oxidant supply means, and
    means for adjusting said second oxidant supply means in response to an adjustment of said sample flow means to maintain the total oxidant supplied to the burner substantially constant.

2. The system according to claim 1 wherein said first and said second oxidant supply means include discrete first and second conduits respectively, said adjusting means for said second oxidant supply means including means for sensing the flow of oxidant through said first conduit and means responsive to said sensing means for adjusting the supply of oxidant through said second conduit to compensate for changes in the supply of oxidant through said first conduit whereby total oxidant flow to the burner remains substantially constant.

3. The system according to claim 2 wherein said sensing means includes a restriction in said first conduit for developing a pressure differential there-across proportional to the flow of oxidant therethrough, pressure monitoring means coupled to said sensing means on opposite sides of said restriction, and means responsive to the pressure monitored by said pressure monitoring means for adjusting the flow of oxidant through said second conduit.

4. The system according to claim 3 including means for providing a reference pressure signal, said adjusting means for said second conduit being responsive to said reference pressure signal and said pressure monitoring means to adjust the flow of oxidant through said second conduit to satisfy the equation $P = A + B - C$, where P is the pressure of the oxidant supplied by said second conduit to the burner, B is the reference signal pressure and A and C are the pressures on the respective opposite sides of the restriction.

5. A gas flow control system for an atomic absorption spectrometer comprising:
   a burner for burning a mixture of fuel, oxidant and sample,
   a mixing chamber for mixing fuel, oxidant and sample,
   means for supplying fuel to said mixing chamber,
   means for supplying a mixture of sample and oxidant to said mixing chamber,
   auxiliary means for supplying oxidant to said mixing chamber,
   means for varying the supply of the sample and oxidant mixture to the mixing chamber, and
   means for adjusting the flow of oxidant through said auxiliary supply means in response to a variation in the supply of oxidant supplied by said sample and oxidant supply means such that the total oxidant flow supplied to said burner remains substantially constant.

6. An automatic gas flow control apparatus for an atomic absorption spectrometer instrument system including means for burning a mixture of fuel, oxidant and an unknown element-containing sample, which comprises:
   means for supplying a predetermined flow of the fuel to the burner means;
   means for introducing a variable flow of sample containing the unknown element to the burner including means adjustable to vary the sample flow so as to optimize the measured signal of said spectrometer, said sample adjusting means including means for supplying oxidant to said burner, the flow of the oxidant supplied to said burner being dependent upon the adjustment made for supplying sample;
   means for supplying a variable flow of oxidant to the burner, the varying flow supplied being equal to the difference between a predetermined total flow of oxidant required for a prescribed sensitivity of the spectrometer and the varying amount supplied by said sample introducing means;
   means for sensing the flow of oxidant supplied to the sample introducing means and to the burner by said variable oxidant supply means;
   means for comparing the sensed flow of oxidant to the sample introducing means and to the burner by said variable oxidant supply means to the predetermined total flow of oxidant required for a prescribed sensitivity of the spectrometer; and
   means for adjusting the flow of oxidant to said burner by said variable oxidant supply means, in response to said comparing means, to compensate for said adjustment to said sample introducing means, whereby the predetermined total flow of oxidant to the burner is maintained substantially constant.

7. The apparatus of claim 6 further comprising a pneumatic computing means including an oxidant inlet port, an oxidant outlet port, pressure command means and pressure monitoring means, said pressure command means being responsive to a command pressure proportional to the predetermined total flow of oxidant desired to the burner, said pressure monitoring means being responsive to said flow sensing means, said computing means being operative in response to said pressure command means and said pressure monitoring means to adjust the flow of oxidant between said inlet port and said outlet port to compensate for variations in the flow of oxidant through said sample introducing means.

8. The apparatus of claim 7 wherein the means for sensing the flow of oxidant supplied to the sample introducing means includes means in line with the oxidant supply to said sample introducing means, said in-line means developing a pressure differential there-across proportional to the flow of oxidant therethrough, said pressure monitoring means including first and second ports connected to respective sides of said in-line means, whereby said computing means in response to said pressure command means and the pressure differential across said in-line means, adjusts the flow of oxidant between said inlet port and said outlet port to satisfy the equation, $P = A + B - C$, where P is the pressure at the oxidant outlet port, B is the command pressure and A and C are the pressures on respective sides of the in-line means.

9. The apparatus of claim 8, wherein said computing means includes means for mechanically adjusting same, whereby the pressure at the oxidant outlet port can be adjusted to assure the lowest required flow rate of oxidant therethrough for the minimum command pressure.

10. The apparatus of claim 8 wherein said in-line means is a restrictor.

11. The apparatus of claim 7 further comprising means for converting an electrical signal symbolizing the predetermined total flow of oxidant required for a prescribed sensitivity of the spectrometer into said command pressure.

12. The apparatus of claim 11 further comprising means for converting an electrical signal symbolizing said predetermined flow of the fuel to said burner means into an equivalent pressure, said apparatus further including means pneumatically responsive to said equivalent pressure to thereby supply said predetermined flow of fuel.

* * * * *